United States Patent [19]
Wilk et al.

[11] Patent Number: 5,776,126
[45] Date of Patent: Jul. 7, 1998

[54] LAPAROSCOPIC SURGICAL APPARATUS AND ASSOCIATED METHOD

[76] Inventors: Peter J. Wilk, 185 West End Ave., New York, N.Y. 10023; Cary W. Schneebaum, 230 Brinckerhoff Ct., Englewood, N.J. 07631

[21] Appl. No.: 125,671

[22] Filed: Sep. 23, 1993

[51] Int. Cl.$^6$ .................................................. A61B 17/39
[52] U.S. Cl. .................................. 606/1; 606/15; 414/1
[58] Field of Search ........................ 414/1, 5, 6; 606/1, 606/15, 49

[56] References Cited

U.S. PATENT DOCUMENTS

| | | | |
|---|---|---|---|
| 3,845,771 | 11/1974 | Vise | 606/49 |
| 4,302,138 | 11/1981 | Zarudiansky | 414/5 |
| 4,655,673 | 4/1987 | Hawkes | 414/5 |
| 4,746,894 | 5/1988 | Zeldman | 414/5 |
| 5,004,391 | 4/1991 | Burdea | 414/6 |
| 5,143,505 | 9/1992 | Burdea et al. | 414/5 |
| 5,184,319 | 2/1993 | Kramer | 414/5 X |

OTHER PUBLICATIONS

Telepresence Master Glove Controler, Intelligent Robots And Computer Vision: Fith In Series (1986) 397 pp. 2–7.

*Primary Examiner*—Michael Peffley
*Attorney, Agent, or Firm*—R. Neil Sudol; Henry D. Coleman

[57] ABSTRACT

A laparoscopic surgical apparatus includes a laparoscopic instrument having a distal end portion insertable through a laparoscopic trocar sleeve into an abdominal cavity of a patient, the distal end portion including a plurality of at least partially opposable articulated manipulating fingers. A glove is provided having a plurality of hollow finger parts, while a position sensing system is operatively connected to the glove for detecting positions and configurations of the hollow finger parts upon insertion of a surgeon's hand into the glove and upon movement the finger parts by the surgeon during a laparoscopic procedure. An actuator assembly is operatively connected to the position sensing system and to the laparoscopic instrument for moving the manipulating fingers thereof to essentially duplicate positions and configurations of the glove finger parts in response to signals from the sensing system.

21 Claims, 3 Drawing Sheets

LAPAROSCOPIC SURGICAL APPARATUS AND ASSOCIATED METHOD

BACKGROUND OF THE INVENTION

This invention relates to a laparoscopic surgical apparatus and an associated laparoscopic surgical technique.

Laparoscopy involves the piercing of the abdominal wall with a trocar and the insertion of a tubular trocar sleeve through the perforation. Upon a withdrawal of the trocar from the sleeve, various instruments may be inserted through the trocar sleeve to perform surgical operations inside the abdomen. Such surgical instruments include laparoscopic graspers, clip-appliers, cauterization devices, etc.

Generally, upon the disposition of the first trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

For these reasons, there is considerable interest in expanding the range, efficacy and applications of laparoscopic surgery. One limitation of laparoscopic, as opposed to conventional surgery, is that surgical operations must be performed exclusively via laparoscopic instruments. In contrast, in conventional open surgery, the surgeon may use his hands to directly manipulate organs of the patient.

OBJECTS OF THE INVENTION

An object of the present invention is to provide a laparoscopic instrument or apparatus.

Another object of the present invention is to provide a laparoscopic apparatus which is versatile.

Another, more particular, object of the present invention is to provide a laparoscopic apparatus which enables the surgeon to make greater use of his or her hands in performing surgical operations inside the patient's abdomen.

A further particular object of the present invention is to provide a laparoscopic apparatus which mimics or duplicates hand movements.

Yet another object of the present invention is to provide a laparoscopic surgical method which facilitates organ manipulation during laparoscopic surgery.

These and other objects of the present invention will be apparent from the drawings and detailed descriptions herein.

SUMMARY OF THE INVENTION

A laparoscopic surgical apparatus comprises, in accordance with the present invention, a laparoscopic instrument having a distal end portion insertable through a laparoscopic trocar sleeve into an abdominal cavity of a patient, the distal end portion including a plurality of at least partially opposable articulated manipulating fingers. A glove is provided having a plurality of hollow finger parts, while a position sensing system is operatively connected to the glove for detecting positions and configurations of the hollow finger parts upon insertion of a surgeon's hand into the glove and upon movement the finger parts by the surgeon during a laparoscopic procedure. An actuator assembly is operatively connected to the position sensing system and to the laparoscopic instrument for moving the manipulating fingers thereof to essentially duplicate positions and configurations of the glove finger parts in response to signals from the sensing system.

According to another feature of the present invention, the surgical apparatus further comprises cauterization componentry operatively connected to the instrument at the distal end portion for cauterizing organic tissues of the patient. The cauterization componentry may include a laser-transmitting optical fiber attached to one of the manipulating fingers and extending to a tip thereof. Alternatively or additionally, the cauterization componentry includes an electrical current conductor attached to one of the manipulating fingers and extending to a tip thereof. For bipolar electrical cauterization, a pair of electrical current conductors are attached to respective manipulating fingers of the laparoscopic instrument and extend to tips thereof.

According to a further feature of the present invention, the apparatus further comprises a pressure sensing system on the manipulating fingers for detecting contact pressures between the manipulating fingers and organs inside the abdominal cavity. A pressure generation mechanism is operatively connected to the glove and the pressure sensing system for applying, in response to the operation of the pressure sensing system, pressures to the surgeon's hand in the glove to simulate, for the surgeon, the pressures on the manipulating fingers. Thus, tactile feedback is provided to the surgeon to enhance the "hands-on" feel and responsiveness of the surgical apparatus.

According to additional features of the present invention, the apparatus further comprises a suction application tube attached to a manipulating finger of the laparoscopic instrument, and/or an irrigator conduit attached to another manipulating finger of the laparoscopic instrument.

A disposable glove may be provided on the distal end portion of the laparoscopic instrument, over the manipulating fingers.

A laparoscopic surgical apparatus comprises, in accordance with a more general conceptualization of the present invention, (a) a laparoscopic instrument having a distal end portion insertable through a laparoscopic trocar sleeve into an abdominal cavity of a patient, the distal end portion including a plurality of at least partially opposable articulated manipulating fingers, (b) a position sensing system for detecting positions and configurations of a surgeon's hand upon movement the hand outside of the patient during a laparoscopic procedure, and (c) an actuator mechanism operatively connected to the sensing system and to the instrument for moving the manipulating fingers to essentially duplicate positions and configurations of the surgeon's hand in response to signals from the sensing system. A glove may be provided for attaching the position sensing system to the surgeon's hand. Alternatively, other, non-contact techniques may be used for monitoring the positions and configurations of the surgeon's fingers. Such non-contact techniques include computer monitoring of video input.

A laparoscopic surgical method comprises, in accordance with the present invention, the steps of (i) providing a laparoscopic instrument having a distal end portion including a plurality of at least partially opposable articulated manipulating fingers, (ii) inserting the distal end portion through a laparoscopic trocar sleeve into an abdominal cavity of a patient, (iii) automatically detecting positions and configurations of a surgeon's fingers upon movement of the surgeon's fingers outside of the patient during a laparoscopic procedure, and (iv) automatically moving the manipulating fingers to essentially duplicate positions and configurations of the surgeon's fingers in response to signals from the sensing system.

According to another feature of the present invention, the method further comprises the step of attaching the position sensing system to the surgeon's hand, e.g., via a glove.

According to a supplemental feature of the present invention, the method also comprises the steps of detecting contact pressures between the manipulating fingers and organs inside the abdominal cavity and automatically applying pressure to the surgeon's hand to simulate, for the surgeon, pressures exerted on the manipulating fingers by organic tissues of the patient during a laparoscopic procedure.

Where cauterization componentry is connected to the instrument at the distal end portion thereof, the cauterization componentry is operated to cauterize organic tissues of the patient inside the abdominal cavity.

Where a suction component is attached to the distal end portion of the instrument, the suction component is operated to apply suction inside the abdominal cavity.

A laparoscopic apparatus in accordance with the present invention is versatile. It enables a surgeon to make greater use of his or her hands in performing surgical operations inside the patient's abdomen during a laparoscopic procedure. It facilitates organ manipulation during laparoscopic surgery.

A further particular object of the present invention is to provide a laparoscopic apparatus which mimics or duplicates hand movements.

DETAILED DESCRIPTION

Figure 1:
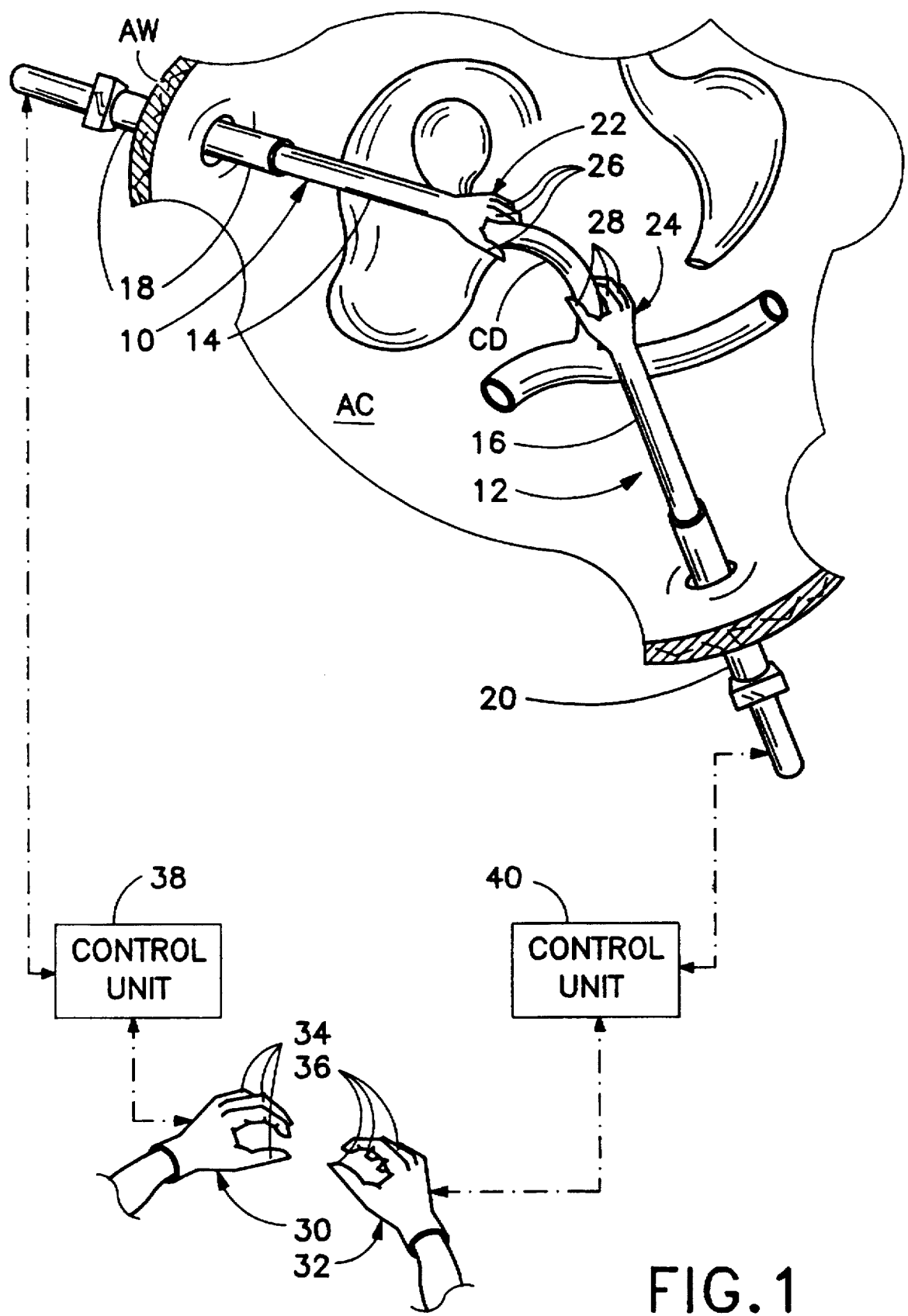
FIG. 1 is partially a schematic perspective view and partially a block diagram of laparoscopic instrumentation in accordance with the present invention, showing insertion of the laparoscopic instrumentation into a patient's abdomen, represented schematically in cross-section.

As illustrated in FIG. 1, a laparoscopic surgical apparatus comprises a pair of laparoscopic instruments 10 and 12 each having a respective distal end portion 14 and 16 insertable through a respective laparoscopic trocar sleeve 18 and 20 into an abdominal cavity AC of a patient. Trocar sleeves 18 and 20 are lodged in an abdominal wall AW of the patient and traverse that wall to be partially disposed inside abdominal cavity AC and partially disposed outside the patient.

Distal end portions 14 and 16 of laparoscopic instruments 10 and 12 each terminate in a respective manipulating device 22 and 24 which essentially has the form and function of a miniature or reduced-scale human hand. Accordingly, each manipulating device 22 and 24 includes a plurality of at least partially opposable articulated manipulating fingers 26 and 28.

As further illustrated in FIG. 1, a pair of gloves 30 and 32 of normal size are provided, each having a plurality of hollow finger parts 34 and 36. Gloves 30 and 32 are operatively connected to laparoscopic instruments 10 and 12, respectively, via control units 38 and 40.

Figure 2:
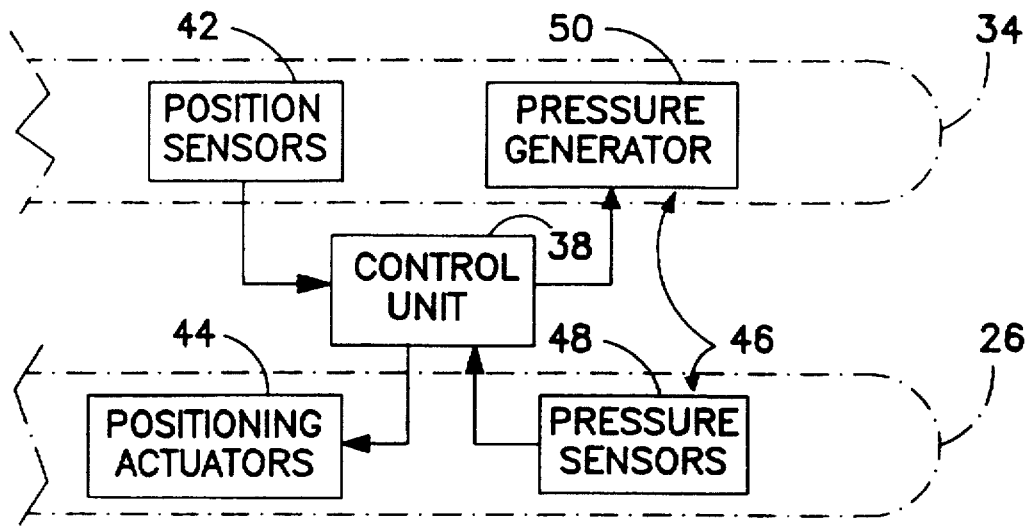
FIG. 2 is a block diagram of functional components of the apparatus of FIG. 1.

As illustrated in FIG. 2, each finger 34 and 36 of gloves 30 and 32 is provided with an array of position and configuration sensors 42. Sensors 42 may take the form of strain gauges connected to gloves 30 and 32 for generating electrical signals which essentially define the positions and configurations of all the fingers 34 or 36 of the respective glove 30 or 32.

In response to the electrical position and configuration coding signals from sensors 42, control unit 38 (or 40) transmits actuator control signals to positioning actuators 44 which are operatively connected to fingers 26 (or 28) of manipulating device 22 (or 24). Positioning actuators 44 may take the form of small hydraulic or pneumatic cylinders or, alternatively, solenoids, which are connected to a mechanical linkage, as is well known in the robotic arts, for controlling the positions and orientations of elements of the linkage.

Upon the insertion of laparoscopic distal end portions 14 and 16 of instruments 10 and 12 through trocar sleeves 18 and 20 at the onset of a laparoscopic surgical procedure, a surgeon inserts his hands into gloves 30 and 32. Gloves 30 and 32 remain outside the abdominal cavity AC of the patient during the entire laparoscopic procedure.

While watching images of the patient's abdominal organs via a conventional video monitor (not illustrated), the surgeon moves his hands inside gloves 30 and 32, thereby deforming the gloves into desired configurations for purposes, for example, of grasping a cystic duct CD (FIG. 1) and separating the duct from other organs in the abdominal cavity AC of the patient. Control units 38 and 40 actuate manipulating devices 22 and 24 of laparoscopic instruments 10 and 12 so that those devices essentially duplicate the configurations of gloves 30 and 32 successively assumed by the action of the surgeon.

The surgical apparatus of FIGS. 1 and 2 further comprises a tactile feedback assembly 46 for providing the surgeon with tactile pressure input in response to the manipulations of internal abdominal organs by manipulating devices 22 and 24. Feedback assembly 46 includes pressure sensors 48 connected to fingers 26 and 28 of manipulating device 22 and 24 for detecting contact pressures between those fingers and organs inside abdominal cavity AC. Pressure sensors 48 may take any form known to the robotic arts, for example, piezoelectric crystals (not shown) or pneumatic pouches (not shown). Pressure sensors 48 are disposed at least along the inner surfaces or pads of fingers 26 and 28.

Pressure sensors 48 are operatively connected to control units 38 and 40 for transmitting electrical pressure encoding signals thereto. Control units 38 and 40 are in turn connected to pressure generators 50 such as piezoelectric crystals (not shown) or pneumatic pouches (not shown) which are operatively connected to fingers 34 and 36 of gloves 30 and 32. In response to signals from controls units 38 and 40, pressure generators 50 apply tactilely sensible pressures to the surgeon's hands in gloves 30 and 32 to simulate, for the surgeon, the pressures on fingers 26 and 28 of manipulating devices 22 and 24. This tactile feedback enhances the surgeon's ability to perform the laparoscopic operation.

Figure 3:
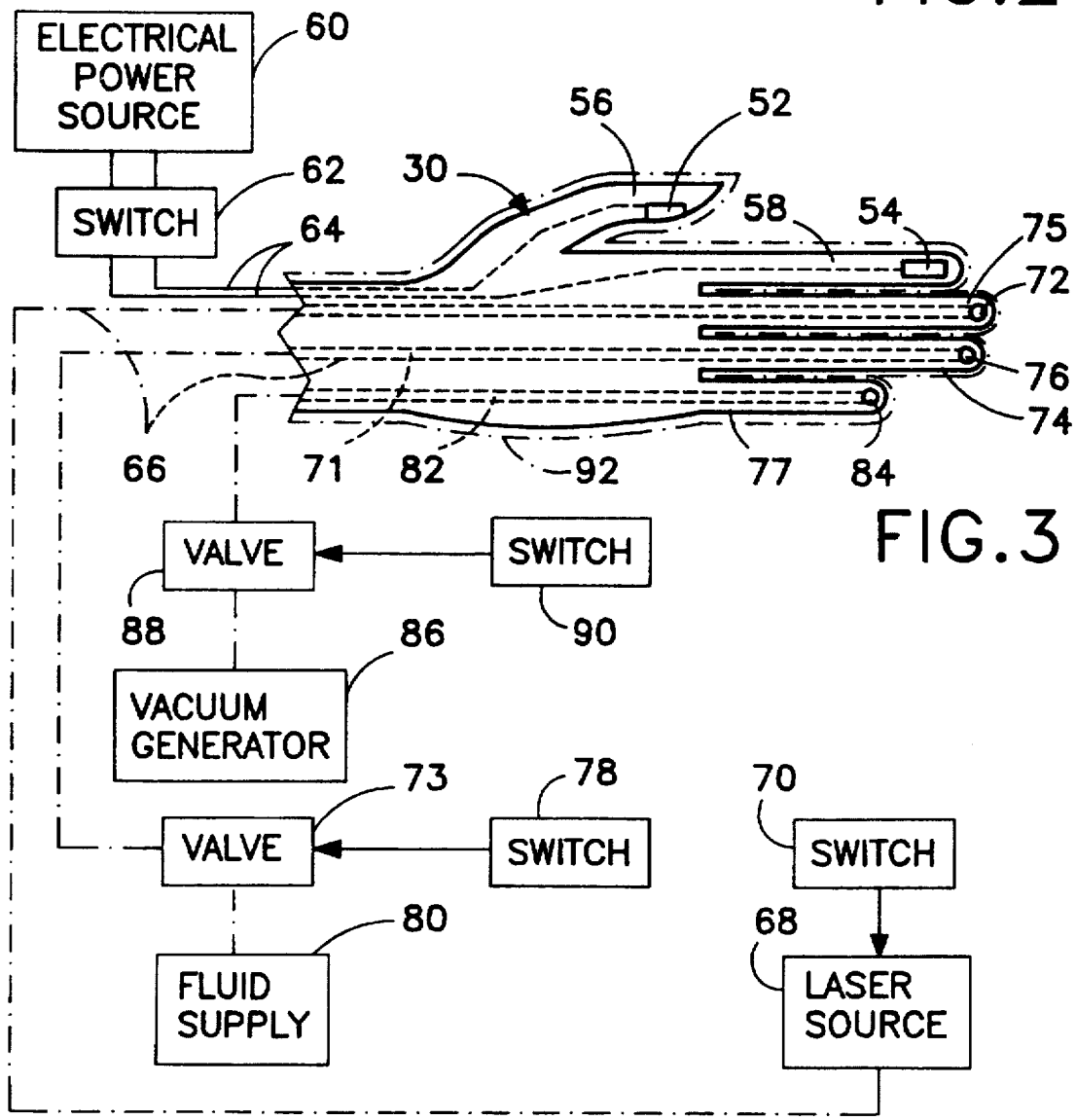
FIG. 3 is partially a schematic elevational view and partially a block diagram of a portion of the laparoscopic instrumentation illustrated in FIG. 1.

As illustrated in FIG. 3, the surgical apparatus further comprises cauterization componentry in the form of electrodes 52 and 54 operatively connected to a thumb 56 and a forefinger 58 of manipulating device 22 or 24. Electrodes 52 and 54 are operatively connected to an electrical power source 60 via a switch 62 and leads 64. Upon the operation of switch 62 (e.g., a foot switch) by the surgeon, a voltage is applied across electrodes 52 and 54. Upon the moving of thumb 56 and forefinger 58 to contact organic abdominal tissues with electrodes 52 and 54, a current flows to cauterize the tissues. Alternatively, a single electrode may be sufficient to conduct cauterizing electrical current through the internal tissues of the patient.

In addition, a finger 26 or 28 of manipulating device 22 or 24 may be provided with an optical fiber 66 which extends from a laser source 68. Upon activation of laser source 68 by operation of a switch 70, a laser beam is transmitted along fiber 66 to a distal tip 72 thereof. Preferably, tip 72 is a contact laser tip, known in the art for enabling the emergence of laser radiation only upon contact between the tip and an object.

As further illustrated in FIG. 3, manipulating device 22 or 24 may be also provided with a built-in or attached conduit or tube 71 extending from a valve 73 along a finger 74 to an outlet port 76. Upon operation of an activation switch 78 by a surgeon operator, valve 73 opens to connect conduit 71 to a pressurized fluid supply 80. Conduit 71 may be used alternately for providing suction to a surgical site. Alternatively, another conduit or tube 82 may be provided in or on manipulating device 22 or 24 for evacuating gases, liquid and particulate matter from a surgical site proximate to an inlet port 84. Conduit 82 extends from inlet port 84 to a vacuum generator 86 via a valve 88. Valve 88 is controlled by a switch 90 operable by a surgeon during a laparoscopic procedure.

Switches 70, 78, and 90 may be foot switches. Alternatively, power source 60, laser source 68, and valves 74 and 88 may be connected to a voice recognition unit (not shown) for activation in response to signals therefrom.

As additionally illustrated in FIG. 3, a disposable glove-like sheath 92 may be disposed over manipulating device 22 or 24. It is to be noted that one or more of the various cauterizing, irrigating components, particularly including electrodes 52 and 54, leads 64, conduits 71 and 82, and ports 76 and 84, may be provided on sheath 92 rather than on manipulating device 22 or 24. In the event that laser-guiding optical fiber 66 remains connected to or embedded in manipulating device 22 or 24, the sheath 92 may be transparent to the laser radiation in a region about the tip of the respective finger.

The cauterization componentry may include a laser-transmitting optical fiber attached to one of the manipulating fingers and extending to a tip thereof. Alternatively or additionally, the cauterization componentry includes an electrical current conductor attached to one of the manipulating fingers and extending to a tip thereof. For bipolar electrical cauterization, a pair of electrical current conductors are attached to respective manipulating fingers of the laparoscopic instrument and extend to tips thereof.

It is to be noted that the componentry of FIG. 3 is optional insofar as additional laparoscopic cauterization instruments, and laparoscopic irrigation and suction instruments (not illustrated) may be inserted through the same or different trocar sleeves as laparoscopic instruments 10 and 12. Such instruments may be configured for manipulation within abdominal cavity AC (FIG. 1) by manipulating device 22 and/or 24 in response to movements of a surgeon's hands in glove 30 and/or 32. Thus, in duplicating surgeon hand motions, manipulating devices 22 and 24 or laparoscopic instruments 10 and 12 may serve as miniature hands manipulating other instruments in abdominal cavity AC.

Figure 4:
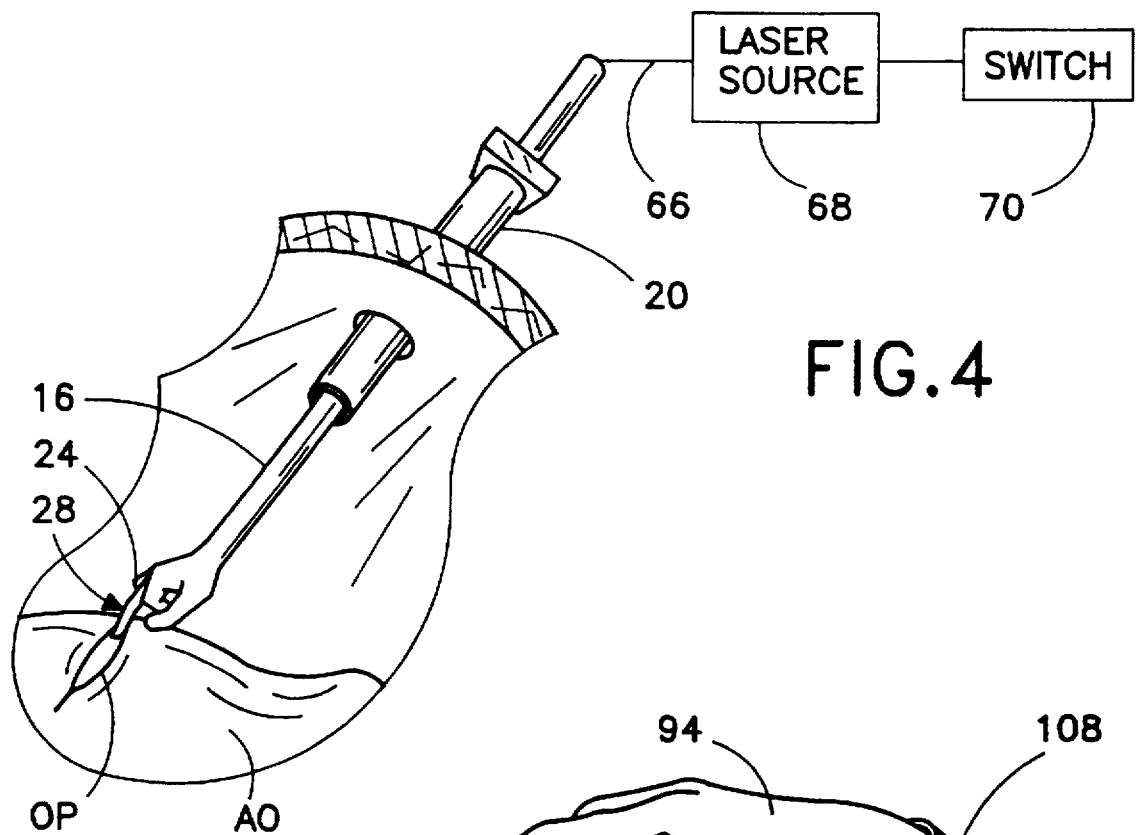
FIG. 4 is partially a schematic perspective view of a laparoscopic instrument in accordance with the present invention and FIG. 5 is partially a partial cross-sectional view of a patient's abdomen, showing a laparoscopic procedure in accordance with the present invention.

FIG. 4 depicts an example in the use of the optional componentry of FIG. 3. A finger 75 with optical fiber 66 is extended while the other fingers are retracted, while switch 70 is operated to activate laser source 68 to close an opening OP in an abdominal organ AO of the patient. A laser beam generated by laser source 68 and transmitted via optical fiber 66 emerges from the extended finger to cauterize the tissues at the surgical site. Bipolar or monopolar electrical cauterization may alternatively be used.

Suction may be applied by extending finger 74 or 77 (FIG. 3) and operating vacuum generate 86 to suck gases through conduit 71 or 82.

Where only one glove 30 or 32 and only one manipulating device 22 or 24 is provided, one of the surgeon's hands is inserted inside the glove for controlling the configurations and relative positions of fingers 26 or 28, while the other hand is used to control the orientation of the respective trocar sleeve 18 or 20 and, hence, of the respective manipulating device 22 or 24, and the degree of insertion of the respective manipulating device 22 or 24 into the patient's abdomen.

Figure 5:
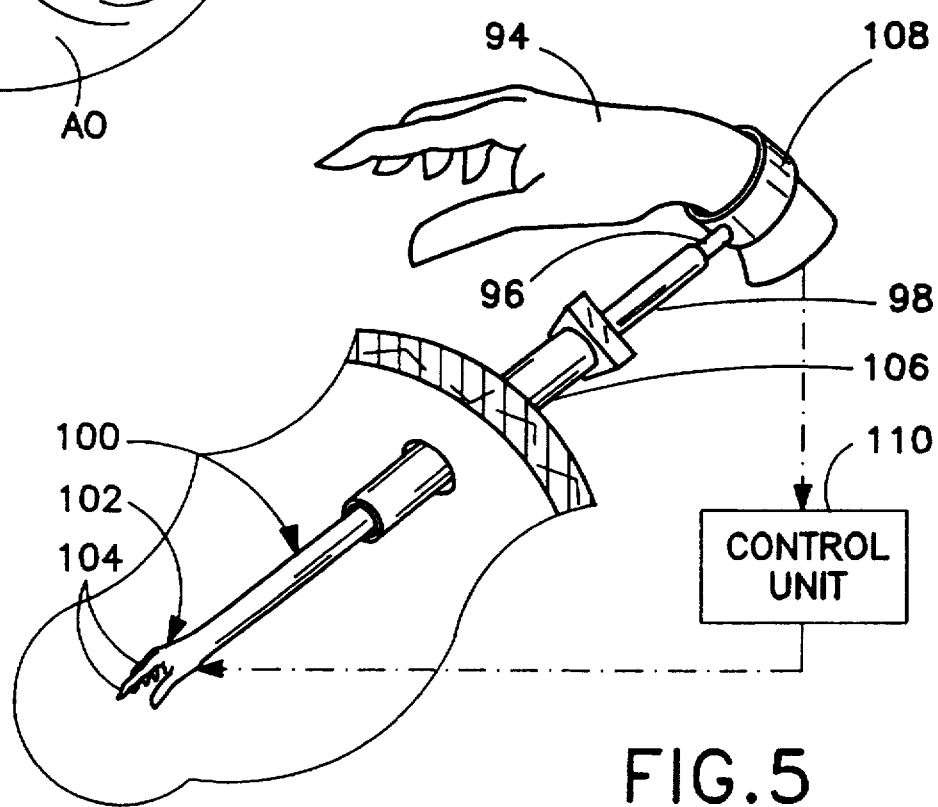

As depicted in FIG. 5, a detector glove 94 is connected via a universal joint 96 to a shaft 98 of a laparoscopic manipulating instrument 100 provided at a distal end with a functional hand-shaped manipulating device 102 having a plurality of fingers 104. The attachment of glove 94 to shaft 98 enables the surgeon to control the degree of insertion of manipulating instrument 98 through a trocar sleeve 106 and also the angle of the trocar sleeve and the instrument shaft 98 with respect to the patient, by simply moving the entire glove 94 with respect to the patient. Universal joint 96 is connected to glove 94 via a substantially rigid collar 108.

Glove 94 may be provided with ancillary surgical componentry as discussed hereinabove with reference to FIG. 3. In addition, a position and configuration sensing system (not shown) in glove 94 is connected via a control unit 110 to position and configuration actuators connected to manipulating device 102.

It is to be noted that the connection of glove 94 to manipulating instrument 100 also provides the surgeon with tactile or kinesthetic information regarding the resistance provided by internal abdominal organs to the insertion and use of manipulating instrument 100.

Although the invention has been described in terms of particular embodiments and applications, one of ordinary skill in the art, in light of this teaching, can generate additional embodiments and modifications without departing from the spirit of or exceeding the scope of the claimed invention. The monitoring of a surgeon's instantaneous hand configuration may be implemented by methods other than the attachment of gloves. For example, a computer may be programmed to analyze electrically encoded video images from two or three cameras. The operating surgeon moves his hands outside the patient but within the field of view of the multiple cameras. In response to video signals from the cameras, the computer determines the positions, orientations and configurations of the surgeon's hands and generates control signals transmitted to manipulating devices 22 and 24 for modifying the positions, orientations and configurations thereof.

Accordingly, it is to be understood that the drawings and descriptions herein are proffered by way of example to facilitate comprehension of the invention and should not be construed to limit the scope thereof.

What is claimed is:

1. A laparoscopic surgical apparatus comprising:
   a laparoscopic instrument having a distal end portion insertable through a laparoscopic trocar sleeve into an abdominal cavity of a patient, said distal end portion including a plurality of at least partially opposable articulated manipulating fingers;
   a glove having a plurality of hollow finger parts;
   position sensing means operatively connected to said glove for detecting positions and configurations of said hollow finger parts upon insertion of a surgeon's hand into said glove and upon movement of said finger parts by said surgeon during a laparoscopic procedure;
   actuator means operatively connected to said sensing means and to said instrument for moving said manipulating fingers to essentially duplicate positions and configurations of said finger parts in response to signals from said sensing means; and
   cauterization means including a laser-transmitting optical fiber for cauterizing organic tissues of the patient, said optical fiber being at least partially connected to said instrument at said distal end portion.

2. The apparatus defined in claim 1 wherein said optical fiber is attached to one of said manipulating fingers and extends to a tip thereof.

3. The apparatus defined in claim 1, further comprising pressure sensing means on said manipulating fingers for detecting contact pressures between said manipulating fingers and organs inside said abdominal cavity, also comprising pressure generation means operatively connected to said glove and said pressure sensing means for applying, in response to the operation of said pressure sensing means, pressures to the surgeon's hand in said glove to simulate, for the surgeon, the pressures on said manipulating fingers.

4. The apparatus defined in claim 1, further comprising means attached to said distal end portion of said instrument for applying suction.

5. The apparatus defined in claim 1, further comprising means attached to said distal end portion of said instrument for delivering irrigation fluid inside said abdominal cavity.

6. The apparatus defined in claim 1, further comprising a glove disposed on said distal end portion over said manipulating fingers.

7. A laparoscopic surgical apparatus comprising:
   a laparoscopic instrument having a distal end portion Insertable through a laparoscopic trocar sleeve into an abdominal cavity of a patient, said distal end portion including a plurality of at least partially opposable articulated manipulating fingers;
   position sensing means for detecting positions and configurations of a surgeon's hand upon movement by said hand outside of the patient during a laparoscopic procedure; and
   actuator means operatively connected to said sensing means and to said instrument for moving said manipulating fingers to essentially duplicate positions and configurations of the surgeon's hand in response to signals from said sensing means; and
   fluid transfer means for conveying fluid between said abdominal cavity and an environment external to the patient, said fluid transfer means being at least partially connected to said instrument at said distal end portion.

8. The apparatus defined in claim 7, further comprising means for attaching said position sensing means to the surgeon's hand.

9. The apparatus defined in claim 8 wherein said means for attaching includes a glove disposable about the surgeon's hand.

10. The apparatus defined in claim 7, also comprising pressure sensing means on said manipulating fingers for detecting contact pressures between said manipulating fingers and organs inside said abdominal cavity, further comprising means attachable to the surgeon's hand and operatively connected to said pressure sensing means for applying pressure to the surgeon's hand to simulate, for the surgeon, pressures exerted on said manipulating fingers by organic tissues of the patient during a laparoscopic procedure.

11. The apparatus defined in claim 7, further comprising cauterization means connected to said instrument at said distal end portion for cauterizing organic tissues of the patient.

12. The apparatus defined in claim 7, wherein said fluid transfer means includes means attached to said distal end portion of said instrument for applying suction.

13. The apparatus defined in claim 7, wherein said fluid transfer means includes means attached to said distal end portion of said instrument for delivering irrigation fluid inside said abdominal cavity.

14. A laparoscopic surgical method comprising the steps of:
   providing a laparoscopic instrument having a distal end portion including a plurality of at least partially opposable articulated manipulating fingers;
   inserting said distal end portion through a laparoscopic trocar sleeve into an abdominal cavity of a patient;
   automatically detecting positions and configurations of a surgeon's fingers upon movement of said surgeon's fingers outside of the patient during a laparoscopic procedure; and
   automatically moving said manipulating fingers to essentially duplicate positions and configurations of the surgeon's fingers in response to signals from said sensing means.

15. The method defined in claim 14, further comprising the step of attaching said position sensing means to the surgeon's hand.

16. The method defined in claim 15 wherein said step of attaching includes the step of disposing a glove about the surgeon's hand.

17. The method defined in claim 14, also comprising the step of detecting contact pressures between said manipulating fingers and organs inside said abdominal cavity, further comprising the step of automatically applying pressure to the surgeon's hand to simulate, for the surgeon, pressures exerted on said manipulating fingers by organic tissues of the patient during a laparoscopic procedure.

18. The method defined in claim 14, further comprising the steps of providing cauterization means connected to said instrument at said distal end portion and operating said cauterization means to cauterize organic tissues of the patient inside said abdominal cavity.

19. The method defined in claim 14, further comprising the steps of automatically detecting contact pressures between said manipulating fingers and organs inside said abdominal cavity and applying pressures to the surgeon's hand outside said abdominal cavity to simulate, for the surgeon, the pressures on said manipulating fingers.

20. The method defined in claim 14, further comprising the steps of providing suction means attached to said distal end portion of said instrument for applying suction and operating said suction means to apply suction inside said abdominal cavity.

21. The method defined in claim 14, further comprising the steps of (i) providing irrigation means attached to said distal end portion of said instrument for delivering irrigation fluid inside said abdominal cavity and (ii) operating said irrigation means during the laparoscopic procedure.

* * * * *